United States Patent [19]

Loewe et al.

[11] 3,996,368

[45] Dec. 7, 1976

[54] ANTHELMINTICALLY ACTIVE 2-CARBALKOXYAMINO-5(6)-PHENYL SULFONYLOXY BENZIMIDAZOLES

[75] Inventors: Heinz Loewe, Kelkheim, Taunus; Josef Urbanietz, Schwalbach, Taunus; Dieter Düwel, Hofheim, Taunus; Reinhard Kirsch, Niederjosbach, Taunus, all of Germany

[73] Assignee: Hoechst Aktiengesellschaft, Frankfurt am Main, Germany

[22] Filed: Aug. 26, 1975

[21] Appl. No.: 607,928

[30] Foreign Application Priority Data

Aug. 24, 1974 Germany .......................... 2441201

[52] U.S. Cl. ............................. 424/273; 260/309.2; 260/456 A
[51] Int. Cl.² ...................................... C07D 235/32
[58] Field of Search ................ 260/309.2; 424/273

[56] References Cited

UNITED STATES PATENTS

| 3,929,821 | 12/1975 | Beard et al. | 260/309.2 |
| 3,929,824 | 12/1975 | Beard et al. | 260/309.2 |

FOREIGN PATENTS OR APPLICATIONS

| 809,234 | 6/1974 | Belgium | 260/309.2 |

*Primary Examiner*—Natalie Trousof
*Attorney, Agent, or Firm*—Curtis, Morris & Safford

[57] ABSTRACT

2-Carbalkoxyamino-5(6)-phenyl sulfonyloxy benzimidazoles are disclosed as well as a process for their manufacture. The new compounds are valuable chemotherapeutic agents and are suitable for combating diseases caused by parasites in humans and animals, such as helminths and liver flukes.

5 Claims, No Drawings

ANTHELMINTICALLY ACTIVE 2-CARBALKOXYAMINO-5(6)-PHENYL SULFONYLOXY BENZIMIDAZOLES

This invention relates to anthelmintically active 2-carbalkoxy-amino-5(6)-phenyl-sulfonyloxy benzimidazoles and to a process of their manufacture.

2-Carbalkoxy-amino-benzimidazolyl derivatives carrying alkyl, acyl, phenoxy and phenylthio groups in 5(6)-position are known to possess anthelmintic properties (P. Actor et al., Nature 215, 321 (1967); German Offenlegungsschrift Nos. 2,029,637; 2,264,690 and 2,363,348).

More in particular, the present invention relates to anthelmintically active 2-carbalkoxyamino-5(6)-phenyl sulfonyloxy benyimidazoles of the formula (1)

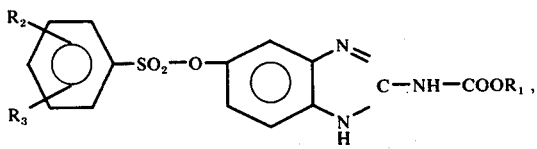

in which $R_1$ stands for alkyl having 1 to 4 carbon atoms, $R_2$ and $R_3$, independently of each other, each stands for hydrogen, hydroxy, alkoxy having 1 to 4 carbon atoms, halogen, trifluoromethyl, alkyl having 1 to 4 carbon atoms, carbalkoxy having 1 to 4 carbon atoms in the alkoxy moiety, or cyano.

The alkyl groups represented by $R_1$, $R_2$ and $R_3$ are methyl, ethyl, propyl, isopropyl, butyl, secondary butyl, and tertiary butyl. The alkoxy groups represented by $R_2$ and $R_3$ are methoxy, ethoxy, propoxy, isopropoxy and butoxy. The halogen atoms represented by $R_2$ and $R_3$ are fluorine, chlorine, bromine and iodine atoms. The carbalkoxy groups represented by $R_2$ and $R_3$ are carbomethoxy, carboethoxy, carbopropoxy or carbobutoxy.

Especially preferred compounds of formula (1) are those in which $R_1$ stands for methyl, ethyl, propyl or butyl, $R_2$ stands for hydrogen or chlorine, and $R_3$ stands for hydrogen, chlorine or trifluoromethyl.

Compounds also provided for by formula (1) are those in which $R_1$ stands for alkyl of 1 to 4 carbon atoms or methyl, $R_2$ stands for hydrogen, and $R_3$ stands for trifluoromethyl.

The present invention also relates to a process for the manufacture of 2-carbalkoxyamino-5(6)-phenylsulfonyloxy benzimidazoles of formula (1) specified above, which comprises condensing an o-phenylene diamine derivative of the formula (2)

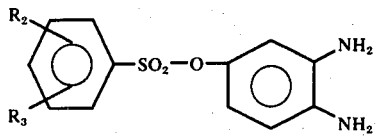

in which $R_2$ and $R_3$ are defined as above, a. with an alkyl-S-methyl-thiourea carboxylate of the formula (3)

in which $R_1$ is defined as above, or b. with a cyanamide carboxylate of the formula (4)

in which $R_1$ is defined as above, in both cases at a pH-value ranging from 1 to 6, preferably from 2 to 5, or c. reacting it with an N-dichloromethylene carbamic acid ester of the formula (5)

in which $R_1$ is defined as above, at a temperature of from $-10°$ to $+40°$ C in the presence of a base, or d. reacting it with a bis-alkyl or bis-aryl-thio-methylene-amino-formate of the formula (6)

in which $R_1$ is defined as above, and $R_4$ and $R_5$, which may be the same or different, each stand for alkyl having 1 to 4 carbon atoms, alkenyl having 3 to 5 carbon atoms, cyclohexyl, or an optionally substituted phenyl or benzyl group of the formula (7) or (8)

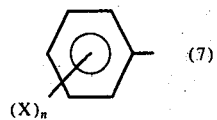 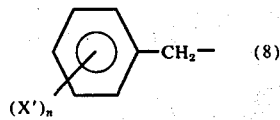

in which X and X', independently of each other, each stand for halogen, methyl or nitro, or $R_4$ and $R_5$ may be linked to form a ring containing 2 or 3 methylene groups, and in which n stands for zero or the integer 1 or 2.

The reactions may also be illustrated by the following reaction schemes:

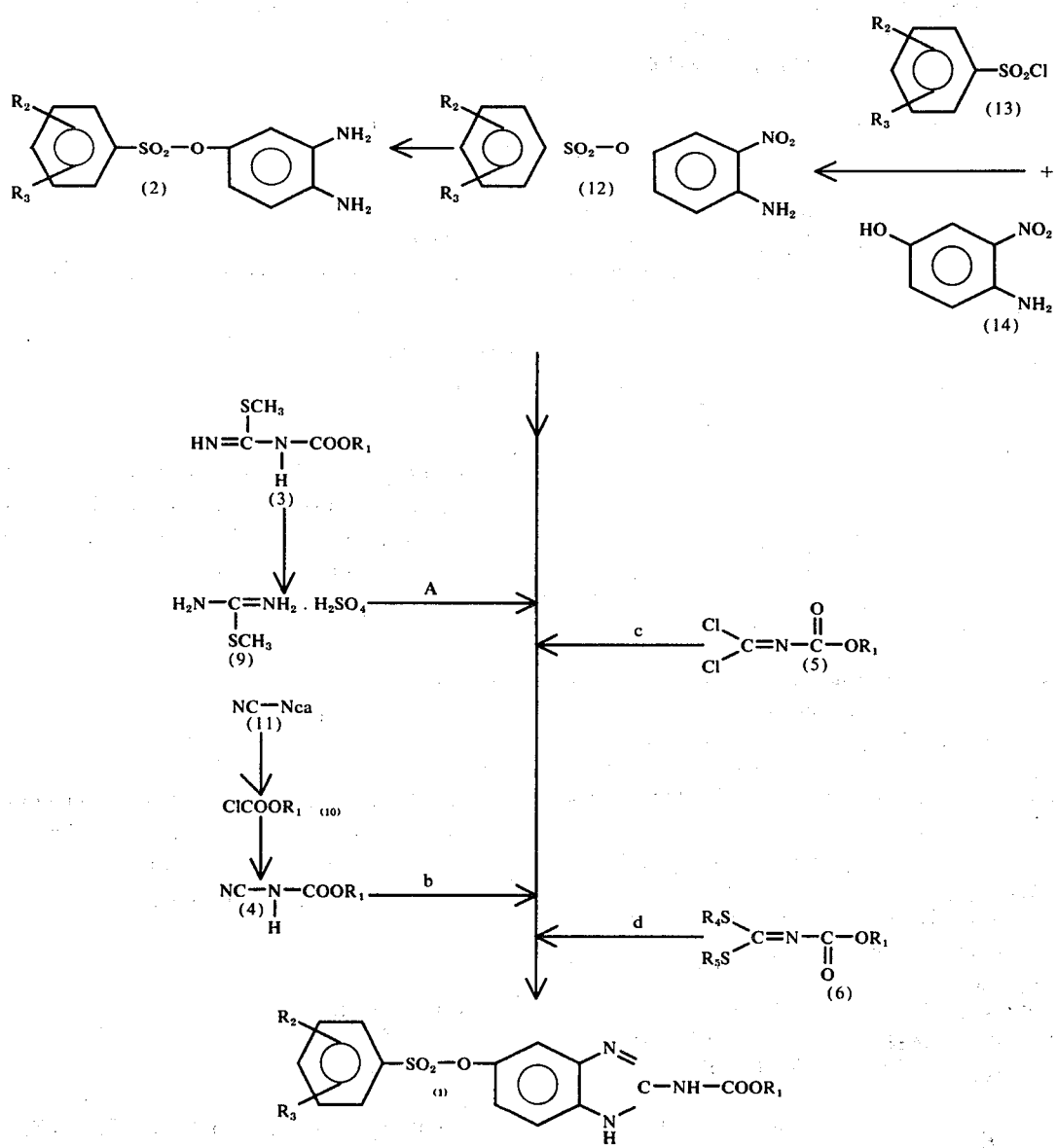

According to reaction method (a), S-methyl-thiourea sulfate of formula (9) is first mixed with a chloroformate of formula (10, in which $R_1$ is defined as in formula (1), in water, then a strong base is added dropwise, for example a 25 % sodium hydroxide solution, while maintaining the temperature low, preferably at about 0° C. The alkyl-S-methyl-thiourea carboxylate of formula (3) which had formed need not be isolated.

As chloroformates of formula (10), there may be mentioned, for example,
methyl chloroformate,
ethyl chloroformate,
propyl chloroformate,
isopropyl chloroformate,
butyl chloroformate,
isobutyl chloroformate,
tert.butyl chloroformate.

The pH-value of the above-cited reaction mixture is then advantageously adjusted to a range of from 2 to 5, suitably by adding an organic acid, such as acetic acid or lactic acid. The o-phenylene diamine derivative of formula (2) is then added, either in the form of a free base or of the acid addition salt, for example the hydrochloride. In this latter case, it may be advantageous to add an alkali metal salt of an organic acid as a buffer.

As o-phenylene diamine derivatives of formula (2), there are mentioned, for example,
benzene sulfonic acid-3,4-diamino-phenyl ester
4-Chloro-benzene sulfonic acid-3,4-diamino-phenyl ester
3-chloro-benzene sulfonic acid-3,4-diamino-phenyl ester
2-chloro-benzene sulfonic acid-3,4-diamino-phenyl ester
2,5-dichloro-benzene sulfonic acid-3,4-diamino-phenyl ester
3,5-dichloro-benzene sulfonic acid-3,4-diamino-phenyl ester
4-bromo-benzene sulfonic acid-3,4-diamino-phenyl ester
3-bromo-benzene sulfonic acid-3,4-diamino-phenyl ester 2-bromo-benzene sulfonic acid-3,4-diamino-phenyl ester
4-methyl-benzene sulfonic acid-3,4-diamino-phenyl ester
3-methyl-benzene sulfonic acid-3,4-diamino-phenyl ester
2-methyl-benzene sulfonic acid-3,4-diamino-phenyl ester
4-tert.butyl-benzene sulfonic acid-3,4-diamino-phenyl ester
2,4-dimethyl-benzene sulfonic acid-3,4-diamino-phenyl ester
2-chloro-4-methyl-benzene sulfonic acid-3,4-diamino-phenyl ester
2-chloro-6-methyl-benzene sulfonic acid-3,4-diamino-phenyl ester
3-chloro-4-methyl-benzene sulfonic acid-3,4-diamino-phenyl ester
3-chloro-6-methyl-benzene sulfonic acid-3,4-diamino-phenyl ester
3-chloro-4-carbethoxy-benzene sulfonic acid-3,4-diamino-phenyl ester
4-chloro-2-methyl-benzene sulfonic acid-3,4-diamino-phenyl ester
4-chloro-3-methyl-benzene sulfonic acid-3,4-diamino-phenyl ester
4-chloro-3,5-dimethyl-benzene sulfonic acid-3,4-diamino-phenyl ester
3-trifluoromethyl-benzene sulfonic acid-3,4-diamino-phenyl ester
4-methoxy-benzene sulfonic acid-3,4-diamino-phenyl ester
3-methoxy-benzene sulfonic acid-3,4-diamino-phenyl ester
2-methoxy-benzene sulfonic acid-3,4-diamino-phenyl ester
4-propoxy-benzene sulfonic acid-3,4-diamino-phenyl ester
4-isopropoxy-benzene sulfonic acid-3,4-diamino-phenyl ester
4-butoxy-benzene sulfonic acid-3,4-diamino-phenyl ester
4-isobutoxy-benzene sulfonic acid-3,4-diamino-phenyl ester.

The reaction components are advantageously reacted at a temperature of from 30° to 100° C within a reaction period of from 30 minutes to 10 hours. Methyl mercaptan is set free as a by-product. The 2-carbalkoxyamino-5(6) phenyl sulfonyloxy benzimidazoles of formula (1) are isolated in the usual manner, for example by diluting the reaction mixture with water and separating the precipitated product by filtration.

In this manner, there are obtained
2-carbomethoxy-5(6)-phenylsulfonyloxy-benzimidazole
2-carbomethoxy-5(6)-(4-chloro-phenylsulfonyloxy)-benzimidazole
2-carbomethoxy-5(6)-(3-chloro-phenylsulfonyloxy)-benzimidazole
2-carbomethoxy-5(6)-(2-chloro-phenylsulfonyloxy)-benzimidazole
2-carbomethoxy-5(6)-(2,5-dichloro-phenylsulfonyloxy)-benzimidazole
2-carbomethoxy-5(6)-(3,5-dichloro-phenylsulfonyloxy)-benzimidazole
2-carbomethoxy-5(6)-(4-bromo-phenylsulfonyloxy)-benzimidazole
2-carbomethoxy-5(6)-(3-bromo-phenylsulfonyloxy)-benzimidazole
2-carbomethoxy-5(6)-(2-bromo-phenylsulfonyloxy)-benzimidazole
2-carbomethoxy-5(6)-(4-methyl-phenylsulfonyloxy)-benzimidazole
2-carbomethoxy-5(6)-(3-methyl-phenylsulfonyloxy)-benzimidazole
2-carbomethoxy-5(6)-(2-methyl-phenylsulfonyloxy)-benzimidazole
2-carbomethoxy-5(6)-(4-tert.butyl-phenylsulfonyloxy)-benzimidazole
2-carbomethoxy-5(6)-(2-chloro-4-methyl-phenylsulfonyloxy)-benzimidazole
2-carbomethoxy-5(6)-(2-chloro-6-methyl-phenylsulfonyloxy)-benzimidazole
2-carbomethoxy-5(6)-(3-chloro-4-methyl-phenylsulfonyloxy)-benzimidazole
2-carbomethoxy-5(6)-(3-chloro-6-methyl-phenylsulfonyloxy)-benzimidazole
2-carbomethoxy-5(6)-(3-chloro-4-carbethoxy-phenylsulfonyloxy)-benzimidazole
2-carbomethoxy-5(6)-(4-chloro-2-methyl-phenylsulfonyloxy)-benzimidazole
2-carbomethoxy-5(6)-(4-chloro-3-methyl-phenylsulfonyloxy)-benzimidazole
2-carbomethoxy-5(6)-(4-chloro-3,5-dimethyl-phenylsulfonyloxy)-benzimidazole
2-carbomethoxy-5(6)-(3-trifluoromethyl-phenylsulfonyloxy)-benzimidazole
2-carbomethoxy-5(6)-(4-methoxy-phenylsulfonyloxy)-benzimidazole
2-carbomethoxy-5(6)-(3-methoxy-phenylsulfonyloxy)-benzimidazole
2-carbomethoxy-5(6)-(2-methoxy-phenylsulfonyloxy)-benzimidazole
2-carbomethoxy-5(6)-(4-propoxy-phenylsulfonyloxy)-benzimidazole
2-carbomethoxy-5(6)-(4-isopropoxy-phenylsulfonyloxy)-benzimidazole
2-carbomethoxy-5(6)-(4-butoxy-phenylsulfonyloxy)-benzimidazole
2-carbomethoxy-5(6)-(4-isobutoxy-phenylsulfonyloxy)-benzimidazole
2-carbethoxyamino-5(6)-phenylsulfonyloxy-benzimidazole
2-carbopropoxyamino-5(6)-phenylsulfonyloxy-benzimidazole
2-carbisopropoxyamino-5(6)-phenylsulfonyloxy-benzimidazole
2-carbobutoxyamino-5(6)-phenylsulfonyloxy-benzimidazole
2-carbisobutoxyamino-5(6)-phenylsulfonyloxy-benzimidazole
2-carbotert.butoxyamino-5(6)-phenylsulfonyloxy-benzimidazole.

According to reaction method (b), a chloroformate of formula (10), as also used for method (a), is first added to an aqueous suspension of cyanamide in the form of a salt, advantageously the calcium salt of formula (11), while maintaining the reaction temperature between 40° and 60° C by cooling.

After filtration of dark-colored by-products which had separated, the cyanamide carboxylate of formula (4) is obtained in the filtrate.

The cyanamide carboxylate of formula (4) thus obtained is combined with an o-phenylene diamine derivative of formula (2), and the pH-value of the mixture is adjusted to a range between 1 to 6, preferably 2 to 4, by adding a mineral acid, for example concentrated hydrochloric acid. To complete the reaction, the reaction mixture is advantageously maintained at a temperature of from 30° to 100° C over a period of 30 minutes to 10 hours, depending on the reactivity of the o-phenylene diamine derivative used. After the reaction mixture has been cooled, the precipitated reaction product of formula (1) is isolated by filtration and washing. The o-phenylene diamine derivative of formula (2) may be used either in the form of a free amine in the manner mentioned above with an alkyl-S-methyl thiourea carboxylate of formula (3) or in the form of an acid addition salt with a suitable inorganic or organic acid, such as hydrochloric acid, sulfuric acid, acetic acid, oxalic acid.

According to the reaction method (c), 1 mol of an o-phenylene-diamine derivative of formula (2) is suitably reacted with 1 mol of an N-dichloromethylene carbamic acid ester of formula (5) in the presence of 2 mols of a base.

As bases, there may be mentioned alkali metal or alkaline earth metal hydroxides, carbonates and hydrogen carbonates, or tertiary organic bases, for example sodium hydroxide, sodium bicarbonate, sodium carbonate, potassium carbonate, potassium bicarbonate, triethylamine, pyridine and methylated pyridines.

The N-dichloromethylene carbamic acid esters of formula (5) may be prepared according to German Offenlegungsschrift No. 1,932,297 by reacting the known dichloromethylene carbamic acid chloride with an alcohol in the presence of an inert organic solvent such as ether, dioxan, tetrahydrofuran, benzene or toluene, at a temperature of from 0° to 40° C.

As examples of N-dichloromethylene carbamic acid esters of formula (5), there may be mentioned N-dichloromethylene carbamic acid methyl ester, as well as the ethyl ester, isopropyl ester, propyl ester, n-butyl ester and sec.-butyl ester thereof.

The reaction temperatures may be varied greatly, generally in the range of from −10° to +60° C, preferably from 0° to 30° C.

According to the reaction method (d), 1 mol of the o-phenylene diamine derivative of formula (2) is advantageously reacted with 1 mol of bis-alkyl or bis-aryl-thiomethylene-amino formate of formula (6) in an inert solvent, such as tetrahydrofuran, dioxan, isopropyl ether or chloroform, at an elevated temperature, advantageously at the boiling temperature of the solvent used.

According to the invention, it is also possible to prepare the bis-alkyl or bis-aryl-thiomethylene-amino-formate of formula (6) in the reaction vessel from the hydrochloride of imino-thiocarbonic acid ester by adding a chloroformate of formula (10), as it is also used for method (a).

In such a case, use has to be made of an acid binder, for example an organic or inorganic base, such as sodium hydroxide, sodium bicarbonate or triethylamine. As a reaction medium, polar and unpolar solvents are suitable, for example ether, acetone, dioxan, water, dimethylformamide, benzene or cyclohexane. During this reaction, the temperature should advantageously not exceed 20° C.

The bis-alkyl or bis-aryl-thiomethylene-amino-formates may be obtained by reacting corresponding dithio-imino-carbonic acid esters with chloroformates of formula (10) according to the method disclosed in U.S. Pat. No. 3,562,290.

As examples of bis-alkyl or bis-aryl-thiomethylene-amino-formates of formula (6), there are mentioned:

bis-methylthio-methylene-amino-formic acid-methyl ester,
bis-methylthio-methylene-amino-formic acid-ethyl ester,
bis-methylthio-methylene-amino-formic acid-propyl ester,
bis-methylthio-methylene-amino-formic acid-isopropyl ester,
bis-methylthio-methylene-amino-formic acid-butyl ester,
bis-methylthio-methylene-amino-formic acid-sec.butyl ester,
bis-butylthio-methylene-amino-formic acid-methyl ester,
methylthio-butylthio-methylene-amino-formic acid-methyl ester,
allylthio-cyclohexylthio-methylene-amino-formic acid-methyl ester,
methylthio-phenylthio-methylene-amino-formic acid-methyl ester,
methylthio-(3,4-dichloro-benzyl-thio)-methylene-amino-formic acid-methyl ester or
methylthio-(2-chloro-4-methylthio)-methylene-amino-formic acid methyl ester.

The o-phenylene diamine derivative of formula (2) used as a starting material is obtained by reduction of a corresponding amino-nitro derivative of formula (12), in which $R_2$ and $R_3$ are defined as in formula (1). The reduction may be carried out, for example by hydrogenation in the presence of Raney nickel and a solvent, such as methanol or dimethylformamide, at a temperature of from 20° to 60° C, or by a treatment with reducing agents, such as sodium dithionite.

The amino-nitro derivatives of formula (12) are obtained by reacting a benzene sulfonic acid chloride of formula (13), in which $R_2$ and $R_3$ are defined as in formula (1), with 3-nitro-4-amino-phenol of formula (14), in an inert solvent in the presence of a base, such as triethylamine.

The 2-carbalkoxyamino-5(6)-phenyl sulfonyloxy benzimidazoles of the invention are valuable chemotherapeutic agents and are suitable for combating diseases caused by parasites in humans and animals, as helminths and liver flukes.

They are especially active against a great number of helminths, for example Haemonchus, Trichostrongylus, Ostertagia, Strongyloides, Cooperia, Chabertia, Oesophagostomum, Hyostrongylus, Ankylostoma, Askaris and Heterakis. Expecially marked is the activity against gastro-intestinal Strongylides, which most especially infest ruminants. The infestation of animals by these parasites causes great economic damage, so that the compounds of the present invention are mainly used in veterinary drugs.

The compounds of the formula (1) can be administered in doses of from 0.5 to 50 mg per kg of body weight for 1 to 14 days, depending on the individual case.

For oral administration, tablets, dragees, capsules, powder, granules or pastes, which contain the active substances in conjunction with the usual excipients and adjuvants for example starch, cellulose powder, talcum, magnesium stearate, sugar, gelatin, calcium carbonate, finely divided silicic acid, carboxymethyl cellulose and similar substances may be used.

For parenteral administration, solutions may be used for example oily solutions prepared using sesame oil, castor oil or synthetic triglycerides, optionally with the addition of tocopherol as an antioxidant and/or surface-active substances, such as sorbitan fatty acid esters. In addition, aqueous suspensions are used which are prepared using ethoxylated sorbitan fatty acid esters, optionally with an addition of thickeners, such as polyethylene glycol or carboxymethyl cellulose.

The concentrations of the compounds of the present invention in the compositions prepared therewith are preferably in the range of from 2 to 20 % by weight for veterinary drugs; for use as medicaments for humans, the concentrations of the active substances are preferably in the range of from 20 to 80 % by weight.

The activity of the compounds of the invention was determined with the aid of chemotherapeutic investigations made on lambs, each have a weight of about 30 kg, which had been infested for test purposes with larvae of *Haemonchus contortus* and *Trichostrongylus colubriformis* respectively. The test animals were kept in tiled boxes which were cleaned thoroughly ever day. After the prepatency period (i.e. time between infestation and sexual maturity of the parasites, when secretion of eggs or larvae begins), the number of eggs per gram of excrement was determined by the modified McMaster method according to Wetzel (Tieraerztliche Umschau, 6, 209 – 210 (1951)). Immediately after this, the treatment of the sheep was started (generally 4 to 8 animals, at least 2 animals, per active substance). The dosage units of the products of the invention were administered to the animals in the form of a suspension each in 10 ml of a 1% tylose suspension. On the 7th, 14th and 28th day after this treatment, the number of eggs per gram of excrement was again determined according to this above-cited method, and its decrease in percentage as compared to the initial value prior to the treatment was calculated.

The products of the invention have an excellent activity not only when administered per os but also parenterally at doses as low as 2 mg/kg of body weight. Therefore, they are by far superior to comparable benzimidazole derivatives, especially to all the known 2-benzimidazolyl carbamates substituted in the 5(6)-position.

The following Examples illustrate the invention.

Process (a)

EXAMPLE 1

47.7 Grams of a 25 % sodium hydroxide solution were added dropwise while cooling with ice at a temperature not exceeding 10° C to a thoroughly stirred mixture of 22.2 g of S-methylthiourea sulfate in 35 ml of water and 10.2 ml of methyl chloroformate. Stirring was continued for half an hour, and then a mixture of 17 ml of glacial acetic acid and 100 ml of water was added.

Subsequently, 15.8 g of benzene sulfonic acid 3,4-diamino phenyl ester dissolved in 100 ml of isopropanol were added, and the mixture was refluxed for 2 hours, whereupon a solid began to precipitate after a short time. The solid was suction-filtered, carefully washed with methanol and then with water. The crude product was purified by recrystallizing it twice from glacial acetic acid/methanol. The yield of pure 2-carbomethoxyamino-5(6)-phenyl sulfonyloxy benzimidazole was 9.6 g having a decomposition point of 242° C.

The benzene-sulfonic acid 3,4-diamino phenyl ester was prepared by hydrogenating 17.5 g of benzene sulfonic acid 3-nitro-4-amino phenyl ester in 200 ml of dimethylformamide with a special nickel catalyst (so-called Ruhr-catalyst) at room temperature under an excess pressure of 50 atmospheres of hydrogen. The catalyst was then separated by filtration and the solvent was removed in vacuo. The residue consisted of benzene sulfonic acid 3,4-diamino phenyl ester and was used directly for ring closure without further purification.

To prepare the benzene sulfonic acid 3-nitro-4-aminophenyl ester, 15.4 g of 3-nitro-4-amino-phenol in 100 ml of acetone were mixed with 14 ml of triethylamine, and a solution of 17.6 g of benzene sulfonic acid chloride in 30 ml of acetone was added dropwise while stirring at a temperature not exceeding an internal temperature of 20° C in an ice bath. Stirring was continued for 3 hours at room temperature, the triethylamine hydrochloride was separated by suction-filtration and the filtrate was evaporated to dryness. The product was stirred with 50 ml of methanol and suction-filtered. Washing with methanol and drying resulted in 18.2 g of benzene sulfonic acid 3-nitro-4-amino phenyl ester, m.p. 140° C.

In an analogous manner, the following compounds were prepared from correspondingly modified starting materials:

2. Via 4-chloro-benzenesulfonic acid-3-nitro-4-amino-phenyl ester, (m.p. 137° C)
and 4-chloro-benzenesulfonic acid-3,4-diamino-phenyl ester,
the 2-carbomethoxyamino-5(6)-(4-chloro)-phenyl-sulfonyloxy)-benzimidazole, m.p. 230° C (decomp.).

3. Via 3-chloro-benzenesulfonic acid-3-nitro-4-amino-phenyl ester, (m.p. 154° C)
and 3-chloro-benzenesulfonic acid-3,4-diamino-phenyl ester,
the 2-carbomethoxyamino-5(6)-(3-chloro-phenyl-sulfonyloxy)-benzimidazole, m.p. 250° C, (decomp.).

4. Via 2-chloro-benzenesulfonic acid-3-nitro-4-amino-phenyl ester
and 2-chloro-benzenesulfonic acid-3,4-diamino-phenyl ester,
the 2-carbomethoxyamino-5(6)-(2-chloro-phenyl-sulfonyloxy)-benzimidazole.

5. Via 2,5-dichloro-benzenesulfonic acid-3-nitro-4-amino-phenyl ester
and 2,5-dichloro-benzenesulfonic acid-3,4-diamino-phenyl ester
the 2-carbomethoxyamino-5(6)-(2,5-dichloro-phenylsulfonyloxy)-benzimidazole.

6. Via 3,5-dichloro-benzenesulfonic acid-3-nitro-4-amino-phenyl ester, (m.P. 170° )
and 3,5-dichloro-benzenesulfonic acid-3,4-diamino-phenyl ester,
the 2-carbomethoxyamino-5(6)-(3,5-dichloro-phenylsulfonyloxy)-benzimidazole, m.p. 280° C, (decomp.).

7. Via 4-bromo-benzenesulfonic acid-3-nitro-4-amino-phenyl ester
and 4-bromo-benzenesulfonic acid-3,4-diamino-phenyl ester,
the 2-carbomethoxyamino-5(6)-(4-bromo-phenyl-sulfonyloxy)-benzimidazole.

8. Via 3-bromo-benzenesulfonic acid-3-nitro-4-amino-phenyl-ester, (m.p. 158° C)
and 3-bromo-benzenesulfonic acid-3,4-diamino-phenyl ester,
the 2-carbomethoxyamino-5(6)-(3-bromo-phenyl-sulfonyloxy)-benzimidazole, m.p. 242° C, (decomp.).

9. Via 2-bromo-benzenesulfonic acid-3-nitro-4-amino-phenyl ester
and 2-bromo-benzenesulfonic acid-3,4-diamino-phenyl ester,
the 2-carbomethoxyamino-5(6)-(2-bromo-phenylsulfonyloxy)-benzimidazole.

10. Via 4-methyl-benzenesulfonic acid-3-nitro-4-amino-phenyl ester, (m.p. 149° C)
and 4-methyl-benzenesulfonic acid-3,4-diamino-phenyl ester,
the 2-carbomethoxyamino-5(6)-(4-methyl-phenylsulfonyloxy)-benzimidazole, m.p. 237° C, (decomp.).

11. Via 3-methyl-benzenesulfonic acid-3-nitro-4-amino-phenyl ester, (m.p. 142° C)
and 3-methyl-benzenesulfonic acid-3,4-diamino-phenyl ester,
the 2-carbomethoxyamino-5(6)-(3-methyl-phenylsulfonyloxy)-benzimidazole, m.p. 250° C, (decomp.).

12. Via 2-methyl-benzenesulfonic acid-3-nitro-4-amino-phenyl ester
and 2-methyl-benzenesulfonic acid-3,4-diamino-phenyl ester,
the 2-carbomethoxyamino-5(6)-(2-methyl-phenylsulfonyloxy)-benzimidazole.

13. Via 4-tert.butyl-benzenesulfonic acid-3-nitro-4-amino-phenyl ester
and 4-tert. butyl-benzenesulfonic acid-3,4-diamino-phenyl ester,
the 2-carbomethoxyamino-5(6)-(4-tert.butyl-phenylsulfonyloxy)-benzimidazole.

14. Via 2,4-dimethyl-benzenesulfonic acid-3-nitro-4-amino-phenyl ester
and 2,4-dimethyl-benzenesulfonic acid-3,4-diamino-phenyl ester,
the 2-carbomethoxyamino-5(6)-(2,4-dimethyl-phenylsulfonyloxy)-benzimidazole.

15. Via 2-chloro-4-methyl-benzenesulfonic acid-3-nitro-4-amino-phenyl ester
and 2-chloro-4-methyl-benzenesulfonic acid-3,4-diamino-phenyl ester,
the 2-carbomethoxyamino-5(6)-(2-chloro-4-methyl-phenyl-sulfonyloxy)-benzimidazole.

16. Via 2-chloro-6-methyl-benzenesulfonic acid-3-nitro-4-amino-phenyl ester
and 2-chloro-6-methyl-benzenesulfonic acid-3,4-diamino-phenyl ester,
the 2-carbomethoxyamino-5(6)-(2-chloro-6-methyl-phenyl-sulfonyloxy)-benzimidazole.

17. Via 3-chloro-4-methyl-benzenesulfonic acid-3-nitro-4-amino-phenyl ester
and 3-chloro-4methyl-benzenesulfonic acid-3,4-diamino-phenyl ester,
the 2-carbomethoxyamino-5(6)-(3-chloro-4-methyl-phenyl-sulfonyloxy)-benzimidazole.

18. Via 3-chloro-6-methyl-benzenesulfonic acid-3-nitro-4-amino-phenyl ester
and 3-chloro-6-methyl-benzenesulfonic acid-3,4-diamino-phenyl ester.
the 2-carbomethoxyamino-5(6)-(3-chloro-6-methyl-phenyl-sulfonyloxy)-benzimidazole.

19. Via 4-chloro-2-methyl-benzenesulfonic acid-3-nitro-4-amino-phenyl ester
and 4-chloro-2-methyl-benzenesulfonic acid-3,4-diamino-phenyl ester,
the 2-carbomethoxyamino-5(6)-(4-chloro-2-methyl-phenyl-sulfonyloxy)-benzimidazole.

20. Via 4-chloro-3-methyl-benzenesulfonic acid-3-nitro-4-amino-phenyl ester
and 4-chloro-3-methyl-benzenesulfonic acid-3,4-diamino-phenyl ester,
the 2-carbomethoxyamino-5(6)-(4-chloro-3-methyl-phenyl-sulfonyloxy)-benzimidazole.

21. Via 4-chloro-3,5-dimethyl-benzenesulfonic acid-3-nitro-4-amino-phenyl ester
and 4-chloro-3,5-dimethyl-benzenesulfonic acid-3,4-diamino-phenyl ester,
the 2-carbomethoxyamino-5(6)-(4-chloro-3,5-dimethyl-phenyl-sulfonyloxy)-benzimidazole.

22. Via 3-trifluoromethyl-benzenesulfonic acid-3-nitro-4-amino-phenyl ester, (m.p. 131° C)
and 3-trifluoromethyl-benzenesulfonic acid-3,4-diamino-phenyl ester,
the 2-carbomethoxyamino-5(6)-(3-trifluoromethyl-phenyl-sulfonyloxy)-benzimidazole, m.p. 215° C (decomp.).

23. Via 4-methoxy-benzenesulfonic acid-3-nitro-4-amino-phenyl ester
and 4-methoxy-benzenesulfonic acid-3,4-diamino-phenyl ester,
the 2-carbomethoxyamino-5(6)-(4-methoxy-phenylsulfonyloxy)-benzimidazole.

24. Via 3-methoxy-benzenesulfonic acid-3-nitro-4-amino-phenyl ester
and 3-methoxy-benzenesulfonic acid-3,4-diamino-phenyl ester,
the 2-carbomethoxyamino-5(6)-(3-methoxy-phenylsulfonyloxy)-benzimidazole.

25. Via 2-methoxy-benzenesulfonic acid-3-nitro-4-amino-phenyl ester
and 2-methoxy-benzenesulfonic acid-3,4-diamino-phenyl ester,
the 2-carbomethoxyamino-5(6)-(2-methoxy-phenylsulfonyloxy)-benzimidazole.

26. Via 4-propoxy-benzenesulfonic acid-3-nitro-4-amino-phenyl ester
and 4-propoxy-benzenesulfonic acid-3,4-diamino-phenyl ester,
the 2-carbomethoxyamino-5(6)-(4-propoxy-phenylsulfonyloxy)-benzimidazole.

27. Via 4-isopropoxy-benzenesulfonic acid-3-nitro-4-amino-phenyl ester
and 4-isopropoxy-benzenesulfonic acid-3,4-diamino-phenyl ester,
the 2-carbomethoxyamino-5(6)-(4-isopropoxy-phenylsulfonyloxy)-benzimidazole.

28. Via 4-butoxy-benzenesulfonic acid-3-nitro-4-amino-phenyl ester
and 4-butoxy-benzenesulfonic acid-3,4-diamino-phenyl ester
the 2-carbomethoxyamino-5(6)-(4-butoxy-phenylsulfonyloxy)-benzimidazole.

29. Via 4-isobutoxy-benzenesulfonic acid-3-nitro-4-amino-phenyl ester
and 4-isobutoxy-benzenesulfonic acid-3,4-diamino-phenyl ester,
the 2-carbomethoxyamino-5(6)-(4-isobutoxy-phenyl-sulfonyloxy)-benzimidazole.

30. Via 3-cyano-benzenesulfonic acid-3-nitro-4-amino-phenyl ester
and 3-cyano-benzenesulfonic acid-3,4-diamino-phenyl ester,
the 2-carbomethoxyamino-5(6)-(3-cyano-phenylsulfonyloxy)-benzimidazole.

31. Via benzenesulfonic acid-3-nitro-4-amino-phenyl ester
and benzenesulfonic acid-3,4-diamino-phenyl ester, the 2-carbethoxyamino-5(6)-phenylsulfonyloxy-benzimidazole.

32. Via benzenesulfonic acid-3-nitro-4-amino-phenyl ester
    and benzenesulfonic acid-3,4-diamino-phenyl ester, the 2-carbopropoxyamino-5(6)-phenylsulfonyloxy-benzimidazole.

33. Via benzenesulfonic acid-3-nitro-4-amino-phenyl ester
    and benzenesulfonic acid-3,4-diamino-phenyl ester, the 2-carboisopropoxyamino-5(6)-phenylsulfonyloxy-benzimidazole.

34. Via benzenesulfonic acid-3-nitro-4-amino-phenyl ester
    and benzenesulfonic acid-3,4-diamino-phenyl ester, the 2-carbobutoxyamino-5(6)-phenylsulfonyloxy-benzimidazole.

35. Via benzenesulfonic acid-3-nitro-4-amino-phenyl ester
    and benzenesulfonic acid-3,4-diamino-phenyl ester, the 2-carboisobutoxyamino-5(6)-phenylsulfonyloxy-benzimidazole.

36. Via benzenesulfonic acid-3-nitro-4-amino-phenyl ester
    and benzenesulfonic acid-3,4-diamino-phenyl ester, the 2-carbotert.butoxyamino-5(6)-phenylsulfonyloxy-benzimidazole.

37. Via 3,4-dichloro-benzenesulfonic acid-3-nitro-4-amino-phenyl ester, m.p. 149° C
    and 3,4-dichloro-benzenesulfonic acid-3,4-diaminophenyl ester
    the 2-carbomethoxyamino-5(6)-(3,4-dichloro-phenylsulfonyloxy)-benzimidazole, m.p. 255° (decomposition).

38. Via 3-trifluoromethyl-benzenesulfonic acid-3-nitro-4-amino-phenyl ester, m.p. 131° C
    and 3-trifluoromethyl-benzenesulfonic acid-3,4-diamino-phenyl ester
    the 2-carbethoxyamino-5(6)-3(3-trifluoromethyl-phenylsulfonyloxy)-benzimidazole, m.p. 227° C (decomposition).

39. Via 3-trifluoromethyl-benzenesulfonic acid-3-nitro-4-amino ester, m.p. 131° C
    and 3-trifluoromethyl-benzenesulfonic acid-3,4-diamino-phenyl ester
    the 2-carbisopropoxyamino-5(6)-(3-trifluoromethyl-phenyl-sulfonyloxy)benzimidazole, m.p. 205° C (decomposition).

40. Via 3-trifluoromethyl-benzenesulfonic acid-3-nitro-4-amino-phenyl ester, m.p. 131° C
    and 3-trifluoromethyl-benzenesulfonic acid-3,4-diamino-phenyl ester
    the 2-carbisobutoxyamino-5(6)-(3-trifluoromethyl-phenyl-sulfonyloxy)-benzimidazole, m.p. 243° C (decomposition).

Process (b)

EXAMPLE 41

To a solution of 42 g of cyanamide in 210 ml of water, 90 g of chloroformic acid methyl ester and 218 g of a 33% sodium hydroxide solution were added. The mixture was then stirred for 1.5 hours at 30° – 35° C, then a solution of 213 g of benzenesulfonic acid 3,4-diamino phenyl ester in 1 l of isopropanol was added, and the temperature was raised to 80° C. After addition of 200 ml of glacial acetic acid, the reaction mixture was maintained at 90° C for another 3 to 4 hours. It was then allowed to cool and stored overnight in a refrigerator. The precipitated 2-carbomethoxyamino-5(6)-phenylsulfonyloxy-benzimidazole was suction-filtered and washed with isopropanol and water. The crude product was purified by recystallization from glacial acetic acid/methanol. Yield: 80 g, decomposition point: 242° C.

The benzenesulfonic acid 3,4-diamino phenyl ester was obtained as in Example 1 via the benzenesulfonic acid 3-nitro-4-amino phenyl ester which is likewise disclosed in Example 1.

In an analogous manner, the following compounds were prepared using the correspondingly modified starting compounds:

42. Via 3-trifluoromethyl-benzenesulfonic acid-3-nitro-4-amino-phenyl ester, m.p. 131° C
    and 3-trifluoromethyl-benzenesulfonic acid-3,4-diaminophenyl ester
    the 2-carbomethoxyamino-5(6)-3-trifluoromethyl-phenylsulfonyloxy)-benzimidazole, m.p. 215° C (decomposition).

43. Via 3-trifluoromethyl-benzenesulfonic acid-3-nitro-4-amino-phenyl ester, m.p. 131° C
    and 3-trifluoromethyl-benzenesulfonic acid-3,4-diaminophenyl ester
    the 2-carbisopropoxyamino-5(6)-(3-trifluoromethyl-phenyl-sulfonyloxy)-benzimidazole, m.p. 205° C (decomposition).

44. Via 3-trifluoromethyl-benzenesulfonic acid-3-nitro-4-amino-phenyl ester, m.p. 131° C
    and 3-trifluoromethyl-benzenesulfonic acid-3,4-diamino-phenyl ester
    the 2-carbisobutoxyamino-5(6)-(3-trifluoromethyl-phenyl-sulfonyloxy)-benzimidazole, m.p. 243° C (decomposition).

Process (c)

EXAMPLE 45

26.4 Grams of benzenesulfonic acid 3,4-diamino phenyl ester, 20.2 g of triethylamine and 300 ml of chloroform were mixed, and a solution of 15.6 g of N-dichloromethylene carbamic acid methyl ester in 50 ml of chloroform was slowly added while stirring to this mixture at a temperature of at most 20° C. The reaction mixture was stirred for another hour, the precipitate was suction-filtered and washed with chloroform.

For purification, the crude product was recrystallized in glacial acetic acid/methanol, and after suction-filtration it was washed and dried. The yield of 2-carbomethoxyamino-5(6)-phenylsulfonyloxy benzimidazole was 5 g, decomposition point: 242° C.

The benzenesulfonic acid 3,4-diamino-phenyl ester was obtained as in Example 1 from the benzenesulfonic acid 3-nitro-4-amino-phenyl ester which is also disclosed in Example 1.

In an analogous manner, the following compounds were prepared using the correspondingly modified starting materials:

46. Via 3-trifluoromethyl-benzenesulfonic acid-3-nitro-4-amino-phenyl ester, m.p. 131° C
    and 3-trifluoromethyl-benzenesulfonic acid-3,4-diamino-phenyl ester
    the 2-carbomethoxyamino-5(6)-(3-trifluoromethyl-phenylsulfonyloxy)-benzimidazole, m.p. 215° C (decomposition).

47. Via 3-trifluoromethyl-benzenesulfonic acid-3-nitro-4-amino-phenyl ester, m.p. 131° C and 3-trifluoromethyl-benzenesulfonic acid-3,4-diamino-phenyl ester the 2-carbisopropoxyamino-5(6)-(3-trifluoromethyl-phenyl-sulfonyloxy-benzimidazole, m.p. 205° C (decomposition).

48. Via 3-trifluoromethyl-benzenesulfonic acid-3-nitro-4-amino-phenyl ester, m.p. 131° C and 3-trifluoromethyl-benzenesulfonic acid-3,4-diamino-phenyl ester the 2-carbisobutoxyamino-5(6)-(3-trifluoromethyl-phenyl-sulfonyloxy)-benzimidazole, m.p. 243° C (decomposition).

Process (d)

EXAMPLE 49:

17.9 Grams of bis-methylthio-methylene aminoformic acid methyl ester were added to 26.4 g of benzenesulfonic acid 3,4-diamino-phenyl ester in 200 ml of tetrahydrofuran, and the mixture was refluxed for 4 hours. It was then allowed to cool and the precipitated 2-carbomethoxyamino-5(6)-phenylsulfonyloxy-benzimidazole was suction-filtered and purified by recrystallization from glacial acetic acid/methanol. Yield: 12 g, decomposition point: 242° C.

The reaction product was identical with the product obtained according to Example 1.

The benzenesulfonic acid 3,4-diamino phenyl ester was obtained as in Example 1 from the benzenesulfonic acid 3-nitro-4-amino-phenyl ester which is likewise disclosed in Example 1.

EXAMPLE 50

To a cooled solution of 19.7 g of imino-dithiocarbonic acid methyl ester hydrochloride and 12.5 g of chloroformic acid methyl ester in 50 ml of water, a 10% sodium hydroxide solution was added dropwise while taking care that the temperature did not exceed 10° C. As soon as the pH-value had adjusted to 7.5, 26.4 g of benzenesulfonic acid 3,4-diamino phenyl ester in 50 ml of glacial acetic acid were added, and the mixture ws refluxed for 2 hours while stirring. It was then allowed to cool, and the 2-carbomethoxyamino-5(6)-phenyl-sulfonyloxy-benzimidazole formed was suction-filtered. It was identical in its properties with the reaction product disclosed in Example 49.

In an analogous manner, the following compounds were prepared using correspondingly modified starting materials:

51. Via 3-trifluoromethyl-benzenesulfonic acid-3-nitro-4-amino-phenyl ester, m.p. 131° C and 3-trifluoromethyl-benzenesulfonic acid-3,4-diamino-phenyl ester the 2-carbomethoxyamino-5(6)-(3-trifluoromethyl-phenylsulfonyloxy)-benzimidazole, m.p. 215° C (decomposition).

52. Via 3-trifluoromethyl-benzenesulfonic acid-3-nitro-4-amino-phenyl ester, m.p. 131° C and 3-trifluoromethyl-benzenesulfonic acid-3,4-diamino-phenyl ester the 2-carbisopropoxyamino-5(6)-(3-trifluoromethyl-phenyl-sulfonyloxy)-benzimidazole, m.p. 205° C (decomposition).

53. Via 3-trifluoromethyl-benzenesulfonic acid-3-nitro-4-amino-phenyl ester, m.p. 131° C and 3-trifluoromethyl-benzenesulfonic acid-3,4-diamino-phenyl ester the 2-carbisobutoxyamino-5(6)-(3-trifluoromethyl-phenyl-sulfonyloxy)-benzimidazole, m.p. 243° C (decomposition).

We claim:

1. A 2-carbalkoxyamino-5(6) phenylsulfonyloxy benzimidazole of the formula

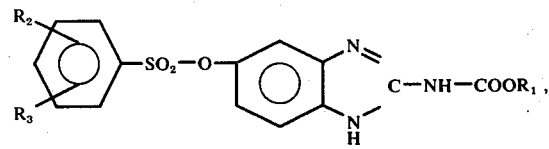

in which $R_1$ stand for alkyl having 1 to 4 carbon atoms, $R_2$ and $R_3$, independently of each other, each stands for hydrogen, hydroxy, alkoxy having 1 to 4 carbon atoms, halogen, trifluoromethyl, alkyl having 1 to 4 carbon atoms, carbalkoxy having 1 to 4 carbon atoms in the alkoxy moiety, or cyano.

2. A compound as claimed in claim 1, wherein $R_1$ stands for alkyl of 1 to 4 carbon atoms, $R_2$ stands for hydrogen, and $R_3$ stands for trifluoromethyl.

3. A compound as claimed in claim 1, wherein $R_1$ is methyl, $R_2$ is hydrogen and $R_3$ is trifluoromethyl.

4. A pharmaceutical composition for combatting helminths and liver flukes, said composition containing an effective amount of a compound as in claim 1 as the active ingredient, in admixture or conjunction with a pharmaceutically acceptable carrier.

5. A method for combatting helminths and liver flukes in humans and animals which comprises administering an effective amount of a compound as in claim 1.

* * * * *

UNITED STATES PATENT AND TRADEMARK OFFICE
CERTIFICATE OF CORRECTION

PATENT NO. : 3,996,368
DATED : December 7, 1976
INVENTOR(S) : Loewe et al.

It is certified that error appears in the above-identified patent and that said Letters Patent are hereby corrected as shown below:

In the Heading, Item [30], replace

"August 24, 1974" by --August 28, 1974--.

Signed and Sealed this

Twenty-second Day of February 1977

[SEAL]

Attest:

RUTH C. MASON
*Attesting Officer*

C. MARSHALL DANN
*Commissioner of Patents and Trademarks*